United States Patent
Petermann et al.

(10) Patent No.: US 10,214,594 B2
(45) Date of Patent: *Feb. 26, 2019

(54) WATER-SOLUBLE ESTERIFIED CELLULOSE ETHERS HAVING A LOW DEGREE OF NEUTRALIZATION

(71) Applicant: Dow Global Technologies LLC, Midland, MI (US)

(72) Inventors: Oliver Petermann, Hamburg (DE); Matthias Knarr, Nienburg/Weser (DE); Robert B. Appell, Midland, MI (US)

(73) Assignee: DOW GLOBAL TECHNOLOGIES LLC, Midland, MI (US)

(*) Notice: Subject to any disclaimer, the term of this patent is extended or adjusted under 35 U.S.C. 154(b) by 0 days.

This patent is subject to a terminal disclaimer.

(21) Appl. No.: 15/550,097

(22) PCT Filed: Mar. 8, 2016

(86) PCT No.: PCT/US2016/021330
§ 371 (c)(1),
(2) Date: Aug. 10, 2017

(87) PCT Pub. No.: WO2016/148977
PCT Pub. Date: Sep. 22, 2016

(65) Prior Publication Data
US 2018/0072819 A1    Mar. 15, 2018

Related U.S. Application Data

(60) Provisional application No. 62/133,514, filed on Mar. 16, 2015.

(51) Int. Cl.
*A61K 9/48* (2006.01)
*A61K 47/38* (2006.01)
(Continued)

(52) U.S. Cl.
CPC ............ *C08B 13/00* (2013.01); *A23L 33/125* (2016.08); *A61K 9/4816* (2013.01);
(Continued)

(58) Field of Classification Search
None
See application file for complete search history.

(56) References Cited

U.S. PATENT DOCUMENTS

| | | | |
|---|---|---|---|
| 4,226,981 | A | 10/1980 | Onda et al. |
| 4,365,060 | A | 12/1982 | Onda et al. |

(Continued)

FOREIGN PATENT DOCUMENTS

| | | |
|---|---|---|
| EP | 0219426 | 4/1987 |
| WO | 2005115330 | 12/2005 |

(Continued)

OTHER PUBLICATIONS

McGinity, Aqueous Polymeric Coatings for Pharmaceutical Dosage Forms, The University of Texas at Austin, 1989.

(Continued)

*Primary Examiner* — Aradhana Sasan
(74) *Attorney, Agent, or Firm* — Ballard Spahr LLP

(57) ABSTRACT

An esterified cellulose ether comprising aliphatic monovalent acyl groups and groups of the formula —C(O)—R—COOH, R being a divalent hydrocarbon group, has the following properties: i) the degree of neutralization of the groups —C(O)—R—COOH is not more than 0.4, ii) the total degree of ester substitution is from 0.10 to 0.70, and iii) the esterified cellulose ether has a solubility in water of at least 2.0 weight percent at 2 C.

14 Claims, 3 Drawing Sheets

(51) Int. Cl.
*C08B 11/20* (2006.01)
*C08B 13/00* (2006.01)
*A23L 33/125* (2016.01)

(52) U.S. Cl.
CPC ............ *A61K 9/4866* (2013.01); *A61K 47/38* (2013.01); *C08B 11/20* (2013.01); *A23V 2002/00* (2013.01)

(56) References Cited

U.S. PATENT DOCUMENTS

| | | |
|---|---|---|
| 5,776,501 A | 7/1998 | Kokubo et al. |
| 2012/0161364 A1 | 6/2012 | Son et al. |
| 2018/0071396 A1* | 3/2018 | Petermann ............. A61K 47/38 |
| 2018/0072820 A1* | 3/2018 | Petermann ............. C08B 13/00 |

FOREIGN PATENT DOCUMENTS

| | | |
|---|---|---|
| WO | 2011159626 A1 | 12/2011 |
| WO | 2013148154 A1 | 10/2013 |
| WO | 2013154607 A1 | 10/2013 |
| WO | 2013164121 A1 | 11/2013 |
| WO | 2014031419 A1 | 2/2014 |
| WO | 2014031422 A1 | 2/2014 |
| WO | 2014031447 A1 | 2/2014 |
| WO | 2014137777 A1 | 9/2014 |
| WO | 2014137778 A1 | 9/2014 |
| WO | 2014137779 A1 | 9/2014 |

OTHER PUBLICATIONS

Rowe et al., Handbook of Pharmaceutical Excipients, 6th edition, Pharmaceutical Press, 2010.

* cited by examiner

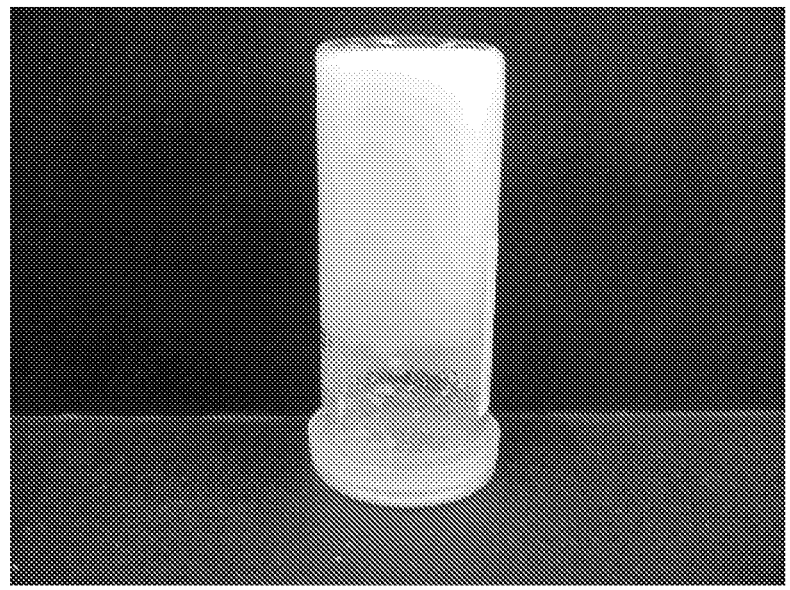
Fig. 3
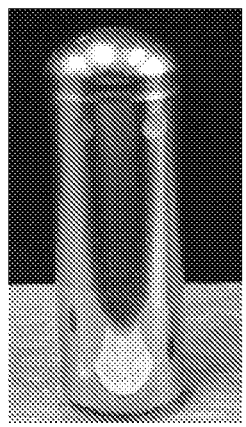 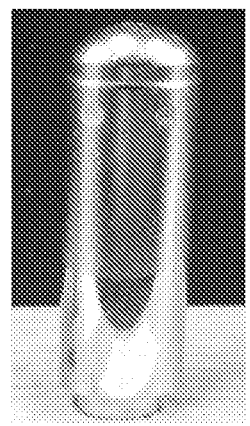 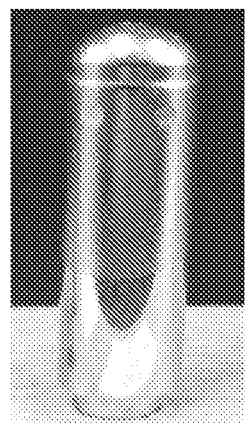
Fig. 4A  Fig. 5A  Fig. 6A
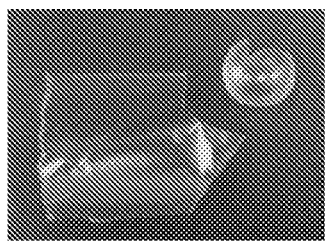  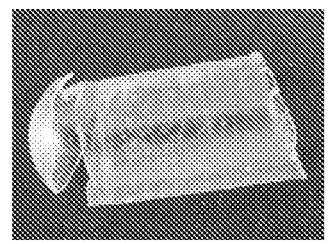
Fig. 4B  Fig. 5B  Fig. 6B

WATER-SOLUBLE ESTERIFIED CELLULOSE ETHERS HAVING A LOW DEGREE OF NEUTRALIZATION

FIELD

This invention concerns novel esterified cellulose ethers and their use for producing capsule shells or for coating dosage forms.

INTRODUCTION

Esters of cellulose ethers, their uses and processes for preparing them are generally known in the art. When the esterified cellulose ethers comprise ester groups which carry carboxylic groups, the solubility of the esterified cellulose ethers in aqueous liquids is typically dependent on the pH. For example, the solubility of hydroxypropyl methyl cellulose acetate succinate (HPMCAS) in aqueous liquids is pH-dependent due to the presence of succinate groups, also called succinyl groups or succinoyl groups. HPMCAS is known as enteric polymer for pharmaceutical dosage forms. In the acidic environment of the stomach HPMCAS is protonated and therefore insoluble. HPMCAS undergoes deprotonation and becomes soluble in the small intestine, which is an environment of higher pH. The pH-dependent solubility is dependent on the degree of substitution of acidic functional groups. The dissolution time of various types of HPMCAS dependent on pH and on the degree of neutralization of HPMCAS is discussed in detail in McGinity, James W. *Aqueous Polymeric Coatings for Pharmaceutical Dosage Forms*, New York: M. Dekker, 1989, pages 105-113. This publication illustrates in FIG. 16 on p. 112 the dissolution time of several grades of HPMCAS, which have different degrees of substitution with succinoyl, acetyl and methoxyl groups, in pure water and in 0.1 NaCl depending on the degree of neutralization of the HPMCAS. Depending on the HPMCAS and the presence or absence of NaCl, HPMCAS is soluble when it has a degree of neutralization between about 0.55 and 1. Below a degree of neutralization of about 0.55, all HPMCAS grades are insoluble in pure water and in 0.1 NaCl.

Dosage forms coated with esterified cellulose ethers such as HPMCAS protect the drug from inactivation or degradation in the acidic environment of the stomach or prevent irritation of the stomach by the drug but release the drug in the small intestine. U.S. Pat. No. 4,365,060 discloses enterosoluble capsules. U.S. Pat. No. 4,226,981 discloses a process for preparing mixed esters of cellulose ethers, such as HPMCAS.

International Patent Application WO 2013/164121 teaches that many techniques for preparing capsules still require the combination of an enteric (acid insoluble) polymer and a conventional non-enteric polymer, require salts or pH regulators leading to water sensitivity or brittleness of the resulting capsule shells, require multiple processing steps, and/or need to be processed in non-aqueous media. To solve these problems, WO 2013/164121 discloses an aqueous composition comprising HPMCAS polymer dispersed in water, wherein the polymer is partially neutralized with at least one alkaline material, such as ammonia, sodium hydroxide, calcium hydroxide, potassium hydroxide, cationic polymers, and mixtures thereof. Unfortunately, the partial neutralization may impact the enteric properties of the capsules. E.g., stomach liquid may diffuse into the capsule upon ingestion when the capsule comprises partially neutralized HPMCAS.

Accordingly, there is still the urgent need to provide novel esterified cellulose ethers which are useful for coating dosage forms or for preparing polymeric capsule shells displaying enteric properties, particularly hard capsule shells. There is the particular need to provide coatings for dosage forms or polymeric capsule shells, which can be produced from aqueous solutions of esterified cellulose ethers but do not require the presence of pH regulators.

Surprisingly, a novel esterified cellulose ether has been found which is soluble in water, but which is resistant to dissolution in the acidic environment of the stomach.

SUMMARY

One aspect of the present invention is an esterified cellulose ether which comprises aliphatic monovalent acyl groups and groups of the formula —C(O)—R—COOH, R being a divalent hydrocarbon group, wherein
  i) the degree of neutralization of the groups —C(O)—R—COOH is not more than 0.4,
  ii) the total degree of ester substitution is from 0.10 to 0.70, and
  iii) the esterified cellulose ether has a solubility in water of at least 2.0 weight percent at 2° C.

Another aspect of the present invention is an aqueous composition which comprises an above-described esterified cellulose ether dissolved in an aqueous diluent.

Yet another aspect of the present invention is a liquid composition which comprises at an above-described esterified cellulose ether and an organic diluent.

Yet another aspect of the present invention is a process for coating a dosage form which comprises the step of contacting an above-mentioned composition with the dosage form.

Yet another aspect of the present invention is a process for the manufacture of capsule shells which comprises the step of contacting an above-mentioned composition with dipping pins.

Yet another aspect of the present invention is a coated dosage form wherein the coating comprises at least one above-described esterified cellulose ether.

Yet another aspect of the present invention is a polymeric capsule shell which comprises at least one above-described esterified cellulose ether.

Yet another aspect of the present invention is a capsule which comprises the above-mentioned capsule shell and further comprises a drug or a nutritional or food supplement or a combination thereof.

Yet another aspect of the present invention is a solid dispersion of at least one active ingredient in at least one above-described esterified cellulose ether.

BRIEF DESCRIPTION OF DRAWINGS

FIG. 3 is a photographical representation of a solution of the esterified cellulose ether of Example 18 in water after the solution has been gelled at 40° C.

FIGS. 4A, 5A and 6A are photographical representations of capsule shells on metallic pins having a temperature of 21° C., 30° C. and 55° C., respectively.

FIGS. 4B, 5B and 6B are photographical representations of pieces of capsule shells formed on metallic pins having a temperature of 21° C., 30° C. and 55° C., respectively, after the capsule shells have been removed from the dipping pins.

DESCRIPTION OF EMBODIMENTS

Figure 1:
FIG. 1 is a photographical representation of solutions of the esterified cellulose ethers of Examples 7-11 in water.

Surprisingly, it has been found that the esterified cellulose ethers of the present invention have a solubility in water of at least 2.0 weight percent at 2° C. Clear or turbid solutions with only a small portion of sediment or in the preferred embodiments even without sediment are obtained at a temperature of 2° C. or below. When the temperature of the prepared solution is increased to 20° C., no precipitation occurs. Moreover, aqueous solutions of most of the esterified cellulose ether of the present invention gel at slightly elevated temperature. This renders the esterified cellulose ether of the present invention very useful in a variety of application, e.g. for producing capsules or for coating dosage forms. The advantages of the esterified cellulose ether of the present invention will be described in more detail below.

The esterified cellulose ether has a cellulose backbone having β-1,4 glycosidically bound D-glucopyranose repeating units, designated as anhydroglucose units in the context of this invention. The esterified cellulose ether preferably is an esterified alkyl cellulose, hydroxyalkyl cellulose or hydroxyalkyl alkylcellulose. This means that in the esterified cellulose ether of the present invention, at least a part of the hydroxyl groups of the anhydroglucose units are substituted by alkoxyl groups or hydroxyalkoxyl groups or a combination of alkoxyl and hydroxyalkoxyl groups. The hydroxyalkoxyl groups are typically hydroxymethoxyl, hydroxyethoxyl and/or hydroxypropoxyl groups. Hydroxyethoxyl and/or hydroxypropoxyl groups are preferred. Typically one or two kinds of hydroxyalkoxyl groups are present in the esterified cellulose ether. Preferably a single kind of hydroxyalkoxyl group, more preferably hydroxypropoxyl, is present. The alkoxyl groups are typically methoxyl, ethoxyl and/or propoxyl groups. Methoxyl groups are preferred. Illustrative of the above-defined esterified cellulose ethers are esterified alkylcelluloses, such as esterified methylcelluloses, ethylcelluloses, and propylcelluloses; esterified hydroxyalkylcelluloses, such as esterified hydroxyethylcelluloses, hydroxypropylcelluloses, and hydroxybutylcelluloses; and esterified hydroxyalkyl alkylcelluloses, such as esterified hydroxyethyl methylcelluloses, hydroxymethyl ethylcelluloses, ethyl hydroxyethylcelluloses, hydroxypropyl methylcelluloses, hydroxypropyl ethylcelluloses, hydroxybutyl methylcelluloses, and hydroxybutyl ethylcelluloses; and those having two or more hydroxyalkyl groups, such as esterified hydroxyethylhydroxypropyl methylcelluloses. Most preferably, the esterified cellulose ether is an esterified hydroxyalkyl methylcellulose, such as an esterified hydroxypropyl methylcellulose.

The degree of the substitution of hydroxyl groups of the anhydroglucose units by hydroxyalkoxyl groups is expressed by the molar substitution of hydroxyalkoxyl groups, the MS(hydroxyalkoxyl). The MS(hydroxyalkoxyl) is the average number of moles of hydroxyalkoxyl groups per anhydroglucose unit in the esterified cellulose ether. It is to be understood that during the hydroxyalkylation reaction the hydroxyl group of a hydroxyalkoxyl group bound to the cellulose backbone can be further etherified by an alkylation agent, e.g. a methylation agent, and/or a hydroxyalkylation agent. Multiple subsequent hydroxyalkylation etherification reactions with respect to the same carbon atom position of an anhydroglucose unit yields a side chain, wherein multiple hydroxyalkoxyl groups are covalently bound to each other by ether bonds, each side chain as a whole forming a hydroxyalkoxyl substituent to the cellulose backbone.

The term "hydroxyalkoxyl groups" thus has to be interpreted in the context of the MS(hydroxyalkoxyl) as referring to the hydroxyalkoxyl groups as the constituting units of hydroxyalkoxyl substituents, which either comprise a single hydroxyalkoxyl group or a side chain as outlined above, wherein two or more hydroxyalkoxy units are covalently bound to each other by ether bonding. Within this definition it is not important whether the terminal hydroxyl group of a hydroxyalkoxyl substituent is further alkylated, e.g. methylated, or not; both alkylated and non-alkylated hydroxyalkoxyl substituents are included for the determination of MS(hydroxyalkoxyl). The esterified cellulose ether of the invention generally has a molar substitution of hydroxyalkoxyl groups in the range 0.05 to 1.00, preferably 0.08 to 0.70, more preferably 0.15 to 0.60, most preferably 0.15 to 0.40, and particularly 0.20 to 0.40.

The average number of hydroxyl groups substituted by alkoxyl groups, such as methoxyl groups, per anhydroglucose unit, is designated as the degree of substitution of alkoxyl groups, DS(alkoxyl). In the above-given definition of DS, the term "hydroxyl groups substituted by alkoxyl groups" is to be construed within the present invention to include not only alkylated hydroxyl groups directly bound to the carbon atoms of the cellulose backbone, but also alkylated hydroxyl groups of hydroxyalkoxyl substituents bound to the cellulose backbone. The esterified cellulose ethers according to this invention generally have a DS(alkoxyl) in the range of 1.0 to 2.5, preferably from 1.2 to 2.2, more preferably from 1.6 to 2.05, and most preferably from 1.7 to 2.05.

Most preferably the esterified cellulose ether is an esterified hydroxypropyl methylcellulose having a DS(methoxyl) within the ranges indicated above for DS(alkoxyl) and an MS(hydroxypropoxyl) within the ranges indicated above for MS(hydroxyalkoxyl).

The esterified cellulose ether of the present invention comprises as ester groups the groups of the formula —C(O)—R—COOH, wherein R is a divalent hydrocarbon group, such as —C(O)—$CH_2$—$CH_2$—COOH, and aliphatic monovalent acyl groups, such as acetyl, propionyl, or butyryl, such as n-butyryl or i-butyryl. Specific examples of esterified cellulose ethers are hydroxypropyl methylcellulose acetate succinate (HPMCAS), hydroxypropyl cellulose acetate succinate (HPCAS), hydroxybutyl methyl cellulose propionate succinate (HBMCPrS), hydroxyethyl hydroxypropyl cellulose propionate succinate (HEHPCPrS), or methyl cellulose acetate succinate (MCAS). Hydroxypropyl methylcellulose acetate succinate (HPMCAS) is the most preferred esterified cellulose ether.

An essential feature of the esterified cellulose ethers of the present invention is their total degree of ester substitution, specifically the sum of i) the degree of substitution of aliphatic monovalent acyl groups and ii) the degree of substitution of groups of formula —C(O)—R—COOH. The total degree of ester substitution is at least 0.10, preferably at least 0.15, more preferably at least 0.20, and most preferably at least 0.25. The total degree of ester substitution is not more than 0.70, generally not more than 0.67, preferably up to 0.65, more preferably up to 0.60, and most preferably up to 0.55 or up to 0.50. In one aspect of the present invention esterified cellulose ethers having a total degree of ester substitution of from 0.10 to 0.65 and particularly from 0.20 to 0.60 are preferred. They have been found to gel at slightly elevated temperatures as described further below. In another aspect of the present invention esterified cellulose ethers having a total degree of ester substitution of from 0.20 to 0.50 and particularly from 0.25 to 0.44 are preferred. Esterified cellulose ethers having a total degree of ester substitution of from 0.25 to 0.44 have been found to form clear solutions in water at a concentration of 2 wt.-%.

The esterified cellulose ethers of the present invention generally have a degree of substitution of aliphatic monovalent acyl groups, such as acetyl, propionyl, or butyryl groups, of at least 0.05, preferably at least 0.10, more preferably at least 0.15, most preferably at least 0.20, and particularly at least 0.25 or at least 0.30. The esterified cellulose ethers generally have a degree of substitution of aliphatic monovalent acyl groups of up to 0.69, preferably up to 0.60, more preferably up to 0.55, most preferably up to 0.50, and particularly up to 0.45 or even only up to 0.40. In one embodiment of the invention the esterified cellulose ethers have a degree of substitution of aliphatic monovalent acyl groups of from 0.25 to 0.69 or from 0.25 to 0.65. In another embodiment of the invention esterified cellulose ethers have a degree of substitution of aliphatic monovalent acyl groups of from 0.10 to 0.38.

The esterified cellulose ethers of the present invention generally have a degree of substitution of groups of formula —C(O)—R—COOH, such as succinoyl, of at least 0.01, preferably at least 0.02, more preferably at least 0.05, and most preferably at least 0.10. The esterified cellulose ethers generally have a degree of substitution of groups of formula —C(O)—R—COOH of up to 0.65, preferably up to 0.60, more preferably up to 0.55, and most preferably up to 0.50 or up to 0.45. In one aspect of the invention the esterified cellulose ethers have a degree of substitution of groups of formula —C(O)—R—COOH of 0.05 to 0.45. In another embodiment of the invention esterified cellulose ethers have a degree of substitution of groups of formula —C(O)—R—COOH of 0.02 to 0.14.

Moreover, the sum of i) the degree of substitution of aliphatic monovalent acyl groups and ii) the degree of substitution of groups of formula —C(O)—R—COOH and iii) the degree of substitution of alkoxyl groups, DS(alkoxyl), generally is not more than 2.60, preferably not more than 2.55, more preferably not more than 2.50, and most preferably not more than 2.45. In one aspect of the invention the sum of i) the degree of substitution of aliphatic monovalent acyl groups and ii) the degree of substitution of groups of formula —C(O)—R—COOH and iii) the DS(alkoxyl) is not more than 2.40. Esterified cellulose ethers having such sum of degrees of substitution generally form clear solutions in water at a concentration of 2 wt.-%. The esterified cellulose ethers generally have a sum of degrees of substitution of i) aliphatic monovalent acyl groups and ii) groups of formula —C(O)—R—COOH and iii) of alkoxyl groups of at least 1.7, preferably at least 1.9, and most preferably at least 2.1.

The content of the acetate and succinate ester groups is determined according to "Hypromellose Acetate Succinate, United States Pharmacopia and National Formulary, NF 29, pp. 1548-1550". Reported values are corrected for volatiles (determined as described in section "loss on drying" in the above HPMCAS monograph). The method may be used in analogue manner to determine the content of propionyl, butyryl and other ester groups.

The content of ether groups in the esterified cellulose ether is determined in the same manner as described for "Hypromellose", United States Pharmacopeia and National Formulary, USP 35, pp 3467-3469.

The contents of ether and ester groups obtained by the above analyses are converted to DS and MS values of individual substituents according to the formulas below. The formulas may be used in analogue manner to determine the DS and MS of substituents of other cellulose ether esters.

$$\% \text{ cellulose backbone} = 100 - \left(\% \text{MeO} * \frac{M(OCH_3) - M(OH)}{M(OCH_3)}\right) - \left(\% \text{HPO} * \frac{M(OCH_2CH(OH)CH_3) - M(OH)}{M(OCH_2CH(OH)CH_3)}\right) - \left(\% \text{Acetyl} * \frac{M(COCH_3) - M(H)}{M(COCH_3)}\right) - \left(\% \text{Succinoyl} * \frac{M(COC_2H_4COOH) - M(H)}{M(COC_2H_4COOH)}\right)$$

$$DS(Me) = \frac{\frac{\% \text{MeO}}{M(OCH_3)}}{\frac{\% \text{cellulose backbone}}{M(AGU)}}$$

$$MS(HP) = \frac{\frac{\% \text{HPO}}{M(HPO)}}{\frac{\% \text{cellulose backbone}}{M(AGU)}}$$

$$DS(Acetyl) = \frac{\frac{\% \text{Acetyl}}{M(Acetyl)}}{\frac{\% \text{cellulose backbone}}{M(AGU)}}$$

$$DS(Succinoyl) = \frac{\frac{\% \text{Succinoyl}}{M(Succinoyl)}}{\frac{\% \text{cellulose backbone}}{M(AGU)}}$$

$M(MeO) = M(OCH_3) = 31.03$ Da $M(HPO) = M(OCH_2CH(OH)CH_3) = 75.09$ Da $M(Acetyl) = M(COCH_3) = 43.04$ Da $M(Succinoyl) = M(COC_2H_4COOH) = 101.08$ Da $M(AGU) = 162.14$ Da $M(OH) = 17.008$ Da $M(H) = 1.008$ Da By convention, the weight percent is an average weight percentage based on the total weight of the cellulose repeat unit, including all substituents. The content of the methoxyl group is reported based on the mass of the methoxyl group (i.e., —OCH$_3$). The content of the hydroxyalkoxyl group is reported based on the mass of the hydroxyalkoxyl group (i.e., —O— alkylene-OH); such as hydroxypropoxyl (i.e., —O—CH$_2$CH(CH$_3$)—OH). The content of the aliphatic monovalent acyl groups is reported based on the mass of —C(O)—R$_1$ wherein R$_1$ is a monovalent aliphatic group, such as acetyl (—C(O)—CH$_3$). The content of the group of formula —C(O)—R—COOH is reported based on the mass of this group, such as the mass of succinoyl groups (i.e., —C(O)—CH$_2$—CH$_2$—COOH).

The esterified cellulose ethers of the present invention generally have a weight average molecular weight $M_w$ of up to 500,000 Dalton, preferably up to 250,000 Dalton, more preferably up to 200,000 Dalton, most preferably up to 150,000 Dalton. and particularly up to 100,000 Dalton. Generally they have a weight average molecular weight $M_w$ of at least 10,000 Dalton, preferably at least 12,000 Dalton, more preferably at least 15,000 Dalton, and most preferably at least 20,000 Dalton, and particularly at least 30,000 Dalton.

The esterified cellulose ethers of the present invention generally have a Polydispersity $M_w/M_n$, i.e., a ratio of weight average molecular weight $M_w$ to number average molecular weight $M_n$, of at least 1.5, typically at least 2.1 and often at least 2.9. Moreover, the esterified cellulose ethers of the present invention generally have a Polydispersity of up to 4.1, preferably of up to 3.9, and most preferably of up to 3.7.

$M_w$ and $M_n$ are measured according to Journal of Pharmaceutical and Biomedical Analysis 56 (2011) 743 using a mixture of 40 parts by volume of acetonitrile and 60 parts by volume of aqueous buffer containing 50 mM $NaH_2PO_4$ and 0.1 M $NaNO_3$ as mobile phase. The mobile phase is adjusted to a pH of 8.0. The measurement of $M_w$ and $M_n$ is described in more details in the Examples.

In the esterified cellulose ether of the present invention the degree of neutralization of the groups —C(O)—R—COOH is not more than 0.4, preferably not more than 0.3, more preferably not more than 0.2, most preferably not more than 0.1, and particularly not more than 0.05 or even not more than 0.01. The degree of neutralization can even be essentially zero or only slightly above it, e.g. up to $10^{-3}$ or even only up to $10^{-4}$. The term "degree of neutralization" as used herein defines the ratio of deprotonated carboxylic groups over the sum of deprotonated and protonated carboxylic groups. i.e., Degree of neutralization=[—C(O)—R—COO$^-$]/[—C(O)—R—COO$^-$+—C(O)—R—COOH].

Another essential property of the esterified cellulose ether of the present invention is its water-solubility. Surprisingly, the esterified cellulose ether of the present invention has a solubility in water of at least 2.0 weight percent at 2° C., i.e., it can be dissolved as an at least 2.0 weight percent solution, preferably at least 3.0 weight percent solution, more preferably at least 5.0 weight percent solution or even at least 10.0 weight solution in water at 2° C. Generally the esterified cellulose ether of the present invention can be dissolved as up to 20 weight percent solution or in the most preferred embodiments even as up to 30 weight percent solution in water at a temperature of 2° C. The term "an x weight percent solution in water at 2° C." as used herein means that x g of the esterified cellulose ether is soluble in (100–x) g of water at 2° C.

When determining the water solubility as described in the Examples section, the esterified cellulose ether of the present invention generally has solubility properties that at least 80 wt. %, typically at least 85 wt. %, more typically at least 90 wt. %, and in most cases at least 95 wt. % of the esterified cellulose ether is soluble in a mixture of 2.5 weight parts of the esterified cellulose ether and 97.5 weight parts of water at 2° C. Typically this degree of solubility is also observed in a mixture of 5 or 10 weight parts of the esterified cellulose ether and 95 or 90 weight parts of water at 2° C. or even in a mixture of 20 weight parts of the esterified cellulose ether and 80 weight parts of water at 2° C.

In more general terms, it has surprisingly been found that the esterified cellulose ether of the present invention, in spite of its low degree of neutralization of the groups —C(O)—R—COOH, is soluble in an aqueous liquid at a temperature of less than 10° C., more preferably less than 8° C., even more preferably 5° C. or less, and most preferably up to 3° C., even when the esterified cellulose ether is blended with an aqueous liquid that does not increase the degree of neutralization of the esterified cellulose ether to more than 0.4 or a preferred range listed above, e.g., when the esterified cellulose ether is blended with only water, such as deionized or distilled water. Clear or turbid solutions with only a small portion of sediment or in the preferred embodiments even without sediment are obtained at 2° C. When the temperature of the prepared solution is increased to 20° C., no precipitation occurs.

Moreover, it has been found that aqueous solutions of an esterified cellulose ether of the present invention having a total degree of ester substitution of from 0.10 to 0.65 and particularly from 0.20 to 0.65 gel at slightly elevated temperature, typically at 30 to 55° C. This renders them very useful in a variety of application, e.g. for producing capsules and for coating dosage forms. Very surprisingly hydroxypropyl methyl cellulose acetate succinates (HPMCAS) are provided by the present invention which gel at slightly elevated temperature when they are dissolved in water although an aqueous solution of the hydroxypropyl methyl cellulose from which the HPMCAS is produced does not gel. Some of the esterified cellulose ether of the present invention, specifically some of the HPMCAS materials of the present invention even are transformed into firm, elastic gels at a slightly elevated temperature as described above. The gelation is reversible, i.e. upon cooling to room temperature (20° C.) or less, depending on the concentration of the HPMCAS, the gel transforms into a liquid aqueous solution.

The aqueous liquid in which the esterified cellulose ether of the present invention is soluble may additionally comprise a minor amount of an organic liquid diluent; however, the aqueous liquid should generally comprise at least 80, preferably at least 85, more preferably at least at least 90, and particularly at least 95 weight percent of water, based on the total weight of the aqueous liquid. The term "organic liquid diluent" as used herein means an organic solvent or a mixture of two or more organic solvents. Preferred organic liquid diluents are polar organic solvents having one or more heteroatoms, such as oxygen, nitrogen or halogen like chlorine. More preferred organic liquid diluents are alcohols, for example multifunctional alcohols, such as glycerol, or preferably monofunctional alcohols, such as methanol, ethanol, isopropanol or n-propanol; ethers, such as tetrahydrofuran, ketones, such as acetone, methyl ethyl ketone, or methyl isobutyl ketone; acetates, such as ethyl acetate; halogenated hydrocarbons, such as methylene chloride; or nitriles, such as acetonitrile. More preferably the organic liquid diluents have 1 to 6, most preferably 1 to 4 carbon atoms. The aqueous liquid may comprise a basic compound, but the degree of neutralization of the groups —C(O)—R—COOH of the esterified cellulose ether in the resulting blend of esterified cellulose ether and aqueous liquid should not be more than 0.4, preferably not more than 0.3 or 0.2 or 0.1, more preferably not more than 0.05 or 0.01, and most preferably not more than $10^{-3}$ or even not more than $10^{-4}$. Preferably the aqueous liquid does not comprise a substantial amount of a basic compound. More preferably, the aqueous diluent does not contain a basic compound. Even more preferably, the aqueous liquid comprises from 80 to 100 percent, preferably 85 to 100 percent, more preferably 90 to 100 percent and most preferably 95 to 100 percent of water, and from 0 to 20 percent, preferably 0 to 15 percent, more preferably 0 to 10 percent, and most preferably 0 to 5 percent of an organic liquid diluent, based on the total weight of the aqueous liquid. Most preferably the aqueous liquid consists of water, e.g., deionized or distilled water.

The esterified cellulose ethers of the present invention generally have a viscosity of up to 200 mPa·s, preferably up to 100 mPa·s, more preferably up to 50 mPa·s, and most preferably up to 5.0 mPa·s, measured as a 2.0 wt.-% solution of the esterified cellulose ether in 0.43 wt.-% aqueous NaOH at 20° C. Generally the viscosity is at least 1.2 mPa·s, more typically at least 1.8 mPa·s, even more typically at least 2.4 mPa·s, and most typically at least 2.8 mPa·s, measured as a 2.0 wt.-% solution of the esterified cellulose ether in 0.43 wt.-% aqueous NaOH at 20° C. The 2.0% by weight solution of the esterified cellulose ether is prepared as described in "Hypromellose Acetate Succinate, United States Pharmacopeia and National Formulary, NF 29, pp. 1548-1550", followed by an Ubbelohde viscosity measurement according to DIN 51562-1:1999-01 (January 1999).

Moreover, the esterified cellulose ethers of the present invention are soluble in acetone and have a reasonably low viscosity. Generally the esterified cellulose ethers of the present invention have a viscosity of up to 500 mPa·s, preferably up to 200 mPa·s, more preferably up to 100 mPa·s, and most preferably up to 50 mPa·s, measured as a 10 wt.-% solution of the esterified cellulose ether in acetone at 20° C. The esterified cellulose ethers of the present invention typically have a viscosity of 10 mPa·s or more, measured as a 10 wt.-% solution of the esterified cellulose ether in acetone at 20° C. Details of the production of the esterified cellulose ethers of the present invention are described in the examples. Some aspects of the production process are described below. The esterified cellulose ether of the present invention can be produced by esterifying a cellulose ether, such as an alkyl cellulose, hydroxyalkyl cellulose or hydroxyalkyl alkylcellulose described further above. The cellulose ethers preferably have a DS(alkoxyl) and/or an MS(hydroxyalkoxyl) as described further above. The cellulose ether used as a starting material in the process of the present invention generally has a viscosity of from 1.2 to 200 mPa·s, preferably from 1.8 to 100 mPa·s, more preferably from 2.4 to 50 mPa·s and in particular from 2.8 to 5.0 mPa·s, measured as a 2 weight-% aqueous solution at 20° C. according to ASTM D2363-79 (Reapproved 2006). Cellulose ethers of such viscosity can be obtained by subjecting a cellulose ether of higher viscosity to a partial depolymerization process. Partial depolymerization processes are well known in the art and described, for example, in European Patent Applications EP 1,141,029; EP 210,917; EP 1,423,433; and U.S. Pat. No. 4,316,982. Alternatively, partial depolymerization can be achieved during the production of the cellulose ethers, for example by the presence of oxygen or an oxidizing agent.

The cellulose ether is reacted with an aliphatic monocarboxylic acid anhydride, such as acetic anhydride, butyric anhydride and propionic anhydride, and with a dicarboxylic acid anhydride, such as succinic anhydride. The molar ratio between the anhydride of an aliphatic monocarboxylic acid and the anhydroglucose units of the cellulose ether generally is from 0.1/1 to 7/1, preferably from 0.3/1 to 3.5/1, and more preferably from 0.5/1 to 2.5/1. The molar ratio between the anhydride of a dicarboxylic acid and the anhydroglucose units of cellulose ether preferably is from 0.1/1 to 2.2/1, preferably from 0.2/1 to 1.2/1, and more preferably from 0.3/1 to 0.8.

The molar number of anhydroglucose units of the cellulose ether utilized in the process can be determined from the weight of the cellulose ether used as a starting material, by calculating the average molecular weight of the substituted anhydroglucose units from the DS(alkoxyl) and MS(hydroxyalkoxyl).

The esterification of the cellulose ether is conducted in an aliphatic carboxylic acid as a reaction diluent, such as acetic acid, propionic acid, or butyric acid. The reaction diluent can comprise minor amounts of other solvents or diluents which are liquid at room temperature and do not react with the cellulose ether, such as aromatic or aliphatic solvents like benzene, toluene, 1,4-dioxane, or tetrahydrofurane; or halogenated $C_1$-$C_3$ derivatives, like dichloro methane or dichloro methyl ether, but the amount of the aliphatic carboxylic acid should generally be more than 50 percent, preferably at least 75 percent, and more preferably at least 90 percent, based on the total weight of the reaction diluent. Most preferably the reaction diluent consists of an aliphatic carboxylic acid. The molar ratio [aliphatic carboxylic acid/anhydroglucose units of cellulose ether] generally is at least 0.7/1, preferably at least 1.2/1, and more preferably at least 1.5/1. The molar ratio [aliphatic carboxylic acid/anhydroglucose units of cellulose ether] is generally up to 10/1, and preferably up to 9/1. Lower ratios, such as up to 7/1 or even only up to 4/1 and under optimized conditions even only up to 2/1 can also be used, which makes optimal use of the amount of reaction diluent needed.

In known esterification processes a cellulose ether is reacted with an aliphatic monocarboxylic acid anhydride and a dicarboxylic acid anhydride in the presence of an alkali metal carboxylate, such as sodium acetate or potassium acetate, as the esterification catalyst. In contrast to the known processes, the esterified cellulose ethers of the present invention are produced in the absence of an esterification catalyst, and in particular in the absence of an alkali metal carboxylate.

The reaction temperature for the esterification is generally from 60° C. to 110° C., preferably from 70° C. to 100° C. The esterification reaction is typically completed within 2 to 8 hours, more typically within 3 to 6 hours. After completion of the esterification reaction, the esterified cellulose ether can be precipitated from the reaction mixture in a known manner, for example as described in U.S. Pat. No. 4,226,981, International Patent Application WO 2005/115330, European Patent Application EP 0 219 426 or International Patent Application WO2013/148154. The precipitated esterified cellulose ether is subsequently washed with an aqueous liquid, preferably at a temperature of from 70 to 100° C. Suitable aqueous liquids are described further above.

Another aspect of the present invention is an aqueous composition comprising one or more of the above described esterified cellulose ethers of the present invention dissolved in an aqueous liquid. The aqueous liquid is a described further above. The esterified cellulose ether of the present invention can be brought into aqueous solution by cooling the aqueous composition to a temperature of −2° C. to less than 10° C., preferably of 0° C. to less than 8° C., more preferably of 0.5° C. to less than 5° C., and most preferably of 0.5° C. to 3° C. The aqueous composition preferably comprises at least 5 wt.-%, more preferably at least 10 wt.-%, and preferably up to 30 wt.-%, more preferably up to 20 wt.-% of the esterified cellulose ether of the present invention, based on the total weight of the aqueous composition.

The aqueous composition comprising one or more of the above described esterified cellulose ethers of the present invention dissolved in an aqueous liquid is particularly useful in the manufacture of capsules which comprises the step of contacting the liquid composition with dipping pins. Partial neutralization of the esterified cellulose ether, which might impact the enteric properties of the esterified cellulose ether, is not needed. Furthermore, the capsules can even be prepared at about room temperature, which results in savings in energy. Typically an aqueous composition having a temperature of less than 23° C., more typically less than 15° C. or in some embodiments less than 10° C. is contacted with dipping pins that have a higher temperature than the aqueous composition and that have a temperature of at least 21° C., typically at least 30° C., and more typically at least 50° C. and generally up to 95° C., preferably up to 75° C. The capsules have enteric properties. The aqueous composition comprising one or more of the above described esterified cellulose ethers dissolved in an aqueous liquid is also useful for coating dosage forms, such as tablets, granules, pellets, caplets, lozenges, suppositories, pessaries or implantable dosage forms.

Another aspect of the present invention is a liquid composition comprising an organic diluent and one or more of the above described esterified cellulose ethers of the present invention. The organic diluent may be present in the liquid composition alone or mixed with water. Preferred organic diluents are described further above. The liquid composition preferably comprises at least 5 wt.-%, more preferably at least 10 wt.-%, and preferably up to 30 wt.-%, more preferably up to 20 wt.-% of the esterified cellulose ether of the present invention, based on the total weight of the liquid composition.

The composition of the present invention comprising an aqueous liquid or an organic diluent as described above and one or more of the above described esterified cellulose ethers is also useful as an excipient system for active ingredients and particularly useful as an intermediate for preparing an excipient system for active ingredients, such as fertilizers, herbicides or pesticides, or biologically active ingredients, such as vitamins, herbals and mineral supplements and drugs. Accordingly, the composition of the present invention preferably comprises one or more active ingredients, most preferably one or more drugs. The term "drug" is conventional, denoting a compound having beneficial prophylactic and/or therapeutic properties when administered to an animal, especially humans. In another aspect of the invention the composition of the present invention is used for producing a solid dispersion comprising at least one active ingredient, such as a drug, at least one esterified cellulose ether as described above and optionally one or more adjuvants. A preferred method of producing a solid dispersion is by spray-drying. Spray-drying processes and spray-drying equipment are described generally in Perry's Chemical Engineers' Handbook, pages 20-54 to 20-57 (Sixth Edition 1984). Alternatively, the solid dispersion of the present invention may be prepared by i) blending a) at least one esterified cellulose ether defined above, b) one or more active ingredients and c) one or more optional additives, and ii) subjecting the blend to extrusion. The term "extrusion" as used herein includes processes known as injection molding, melt casting and compression molding. Techniques for extruding, preferably melt-extruding compositions comprising an active ingredient such as a drug are known and described by Joerg Breitenbach, Melt extrusion: from process to drug delivery technology, *European Journal of Pharmaceutics and Biopharmaceutics* 54 (2002) 107-117 or in European Patent Application EP 0 872 233. The solid dispersion of the present invention preferably comprises a) from 20 to 99.9 percent, more preferably from 30 to 98 percent, and most preferably from 60 to 95 percent of an esterified cellulose ether a) as described above, and b) preferably from 0.1 to 80 percent, more preferably from 2 to 70 percent, and most preferably from 5 to 40 percent of an active ingredient b), based on the total weight of the esterified cellulose ether a) and the active ingredient b). The combined amount of the esterified cellulose ether a) and the active ingredient b) is preferably at least 70 percent, more preferably at least 80 percent, and most preferably at least 90 percent, based on the total weight of the solid dispersion. The remaining amount, if any, consists of one or more of the adjuvants c) as described below. Once the solid dispersion comprising at least one active ingredient in at least one esterified cellulose ether has been formed, several processing operations can be used, such as drying, granulation, and milling, to facilitate incorporation of the dispersion into a dosage form, such as strands, pellets, granules, pills, tablets, caplets, microparticles, fillings of capsules or injection molded capsules or in the form of a powder, film, paste, cream, suspension or slurry.

The aqueous composition, the liquid composition comprising an organic diluent and the solid dispersion of the present invention may further comprise optional adjuvants, such as coloring agents, pigments, opacifiers, flavor and taste improvers, antioxidants, and any combination thereof.

Some embodiments of the invention will now be described in detail in the following Examples.

EXAMPLES

Unless otherwise mentioned, all parts and percentages are by weight. In the Examples the following test procedures are used.

Content of Ether and Ester Groups

The content of ether groups in the esterified cellulose ether is determined in the same manner as described for "Hypromellose", United States Pharmacopeia and National Formulary, USP 35, pp 3467-3469.

The ester substitution with acetyl groups (—CO—CH$_3$) and the ester substitution with succinoyl groups (—CO—CH$_2$—CH$_2$—COOH) are determined according to Hypromellose Acetate Succinate, United States Pharmacopia and National Formulary, NF 29, pp. 1548-1550". Reported values for ester substitution are corrected for volatiles (determined as described in section "loss on drying" in the above HPMCAS monograph).

Determination of $M_w$ and $M_n$ $M_w$ and $M_n$ are measured according to Journal of Pharmaceutical and Biomedical Analysis 56 (2011) 743 unless stated otherwise. The mobile phase was a mixture of 40 parts by volume of acetonitrile and 60 parts by volume of aqueous buffer containing 50 mM NaH$_2$PO$_4$ and 0.1 M NaNO$_3$. The mobile phase was adjusted to a pH of 8.0. Solutions of the cellulose ether esters were filtered into a HPLC vial through a syringe filter of 0.45 μm pore size. The exact details of measuring $M_w$ and $M_n$ are disclosed in the International Patent Application No. WO 2014/137777 in the section "Examples" under the title "Determination of $M_w$, $M_n$ and $M_z$". In all Examples of the invention the recovery rate was at least 96%. In the Comparative Examples the recovery rate was at least 89%.

Water-Solubility

Qualitative Determination:

A 2 wt. percent mixture of HPMCAS and water was prepared by mixing 2.0 g HPMCAS, based on its dry weight, with 98.0 g water under vigorous stirring at 0.5° C. for 16 hours. The temperature of the mixture of HPMCAS and water was then increased to 5° C. The water solubility of the esterified cellulose ether was determined by visual inspection. The determination whether the HPMCAS was water-soluble at 2% at 5° C. or not was done as follows. "Water soluble at 2%—yes" means that a solution without sediment was obtained according to the procedure above. "Water soluble at 2%—no" means that at least a significant portion of the HPMCAS remained undissolved and formed sediment when mixing 2.0 g HPMCAS, based on its dry weight, with 98.0 g water according to the procedure above. "Water soluble at 2%—partially" means that only a small portion of the HPMCAS remained undissolved and formed sediment when mixing 2.0 g HPMCAS, based on its dry weight, with 98.0 g water according to the procedure above.

Quantitative Determination:

2.5 weight parts of HPMCAS, based on its dry weight, were added to 97.5 weight parts of deionized water having a temperature of 2° C. followed by stirring for 6 hours at 2° C. and storing for 16 h at 2° C. A weighed amount of this mixture was transferred to a weighed centrifuge vial; the transferred weight of the mixture was noted as M1 in g. The transferred weight of HPMCAS [M2] was calculated as (transferred weight of mixture in g/100 g*2.5 g). The mixture was centrifuged for 60 min at 5000 rpm (2823 xg, Biofuge Stratos centrifuge from Thermo Scientific) at 2° C. After centrifugation an aliquot was removed from the liquid phase and transferred to a dried weighed vial. The weight of the transferred aliquot was recorded as M3 in g. The aliquot was dried at 105° C. for 12 h. The remaining g of HPMCAS was weighted after drying and recorded as M4 in g.

The term "% water soluble at 2.5%" in Table 2 below expresses the percentage of HPMCAS that is actually dissolved in the mixture of 2.5 weight parts of HPMCAS and 97.5 weight parts of deionized water. It is calculated as (M4/M2)*(M1/M3)*100), which corresponds to (g HPMCAS in liquid aliquot/g HPMCAS transferred to centrifuge vial)*(g mixture transferred to centrifuge vial/g liquid aliquot after centrifugation).

Viscosity of Hydroxypropyl Methyl Cellulose Acetate Succinate (HPMCAS)

The 2.0% by weight solution of the HPMCAS in 0.43 wt. % aqueous NaOH was prepared as described in "Hypromellose Acetate Succinate, United States Pharmacopia and National Formulary, NF 29, pp. 1548-1550". An Ubbelohde viscosity measurement according to DIN 51562-1:1999-01 (January 1999) was carried out. The measurement was done at 20° C. The 2.0% by weight solution of the HPMCAS in 0.43 wt. % aqueous NaOH is listed in Table 2 below as "2.0% viscosity in NaOH" for those Examples and Comparative Examples for which this property had been measured.

The 10 wt.-% solution of HPMCAS in acetone was prepared by mixing 10.0 g HPMCAS, based on its dry weight, with 90.0 g of acetone under vigorous stirring at room temperature. The mixture was rolled on a roller mixer for about 24 hours. The solution was centrifuged at 2000 rpm for 3 minutes using a Megafuge 1.0 centrifuge, commercially available from Heraeus Holding GmbH, Germany. An Ubbelohde viscosity measurement according to DIN 51562-1:1999-01 (January 1999) was carried out. The measurement was done at 20° C.

Gelation Temperature and Gel Strength of Solutions of HPMCAS in Water

A 2% solution of HPMCAS in water was produced by adding, 3 g of milled, ground, and dried HPMCAS (under consideration of the water content of the HPMCAS) to 147 g of water (temperature 20-25° C.) at room temperature while stirring with an overhead lab stirrer at 750 rpm with a 3-wing (wing=2 cm) blade stirrer. The solution was then cooled to about 1.5° C. After the temperature of 1.5° C. was reached the solution was stirred for 120 min at 500 rpms. Each solution was stored in the refrigerator prior to the characterization.

Rheology measurements of 2 wt.-% solutions of the HPMCAS of the present invention in water were conducted with a Haake RS600 (Thermo Fisher Scientific) rheometer with cup and bob fixtures (CC-25). The sample was heated at a rate of 1° C. per minute over a temperature range from 5 to 85° C. with a constant strain (deformation) of 2% and a constant angular frequency of 2 Hz. The measurement collection rate was chosen to be 4 data points/min. The storage modulus G', which was obtained from the rheology measurements, represents the elastic properties of the solution and represents the gel strength in the high temperature region, when the storage modulus G' is higher than the loss modulus G".

The obtained data of the storage modulus G', which was obtained from the oscillation measurements, was first logarithmized and normalized to G' (min) to zero and G' (max) to 100. Linear regression curves were fitted to subsets of these storage modulus data (increments of 5 data points). A tangent was fitted to the steepest slope of the regression curve. The intersection of this tangent with the x-axis is reported as gelation temperature. Details how to determine the gelation temperature are described in International Patent Application WO2015/009796 on pages 18 and 19 in the paragraphs "Determination of the gelation temperature of aqueous compositions comprising methyl cellulose" and in FIG. 1 of WO2015/009796.

The gel strength according to the storage modulus G' at 55° C. was also obtained by this rheology measurement.

Production of HPMCAS of Examples 1-27

Succinic anhydride and acetic anhydride was dissolved at 70° C. in glacial acetic acid. Then hydroxypropyl methyl cellulose (HPMC, water free) was added under stirring. The amounts are listed in Table 1 below. The amount of HPMC is calculated on a dried basis. No amount of sodium acetate was added.

The HPMC had a methoxyl substitution ($DS_M$) and hydroxypropoxyl substitution ($MS_{HP}$) as listed in Table 2 below and a viscosity of 3.0 mPa·s, measured as a 2% solution in water at 20° C. according to ASTM D2363-79 (Reapproved 2006). The weight average molecular weight of the HPMC was about 20,000 Dalton. The HPMC is commercially available from The Dow Chemical Company as Methocel E3 LV Premium cellulose ether.

Then the reaction mixture was heated up to the reaction temperature listed in Table 1 below. The reaction time during which the mixture was allowed to react is also listed in Table 1 below. Then the crude product was precipitated by adding 1-2 L of water having a temperature of 21° C. Subsequently the precipitated product was separated from the mixture by filtration and washed several times with water having the temperature listed in Table 1 below. Then the product was isolated by filtration and dried at 55° C. overnight.

For Example 23 the precipitated reaction mass was split in two halves. The first half was washed with water having a temperature of 21° C. (Example 23). The second half was washed with water having a temperature of 95° C. (Example 23A).

Production of HPMCAS of Comparative Examples

Comparative Examples A-E were produced as described for Examples 1-27, except that sodium acetate was mixed with the other reactants in the amounts listed in Table 1 below. Comparative Examples A-E are for comparative purposes, but have not been described in the prior art.

Comparative Examples CE-11 to CE-16 and Comparative Examples CE-D and CE-E correspond to Examples 11-16 and Comparative Examples D and E of the International Patent Application No. WO 2014/137777. Their production is described in detail in the International Patent Application WO 2014/137777 on pages 22 and 23.

Comparative Example CE-C corresponds to Comparative Example C of the International Patent Application WO/2014/031422. Its production is described in detail in the International Patent Application WO/2014/031422 on page 25.

Comparative Examples CE-H to CE-J

Comparative Examples CE-H to CE-J correspond to Comparative Examples H to J of the International Patent Application No. WO 2014/137777. As disclosed in WO 2014/137777 on page 24 and in International Patent Application WO 2011/159626 on pages 1 and 2, HPMCAS is currently commercially available from Shin-Etsu Chemical Co., Ltd. (Tokyo, Japan), known by the trade name "AQOAT". Shin-Etsu manufactures three grades of AQOAT polymers that have different combinations of substituent levels to provide enteric protection at various pH levels, AS-L, AS-M, and AS-H, typically followed by the designation "F" for fine or "G", such as AS-LF or AS-LG. Their sales specifications are listed in Table 1 on page 2 of WO 2011/159626 and in WO 2014/137777 on page 24. According to the Technical Brochure of Shin-Etsu "Shin-Etsu AQOAT Enteric Coating Agent" edition 04.9 05.2/500, all grades of AQOAT polymers are soluble in 10% NaOH but insoluble in purified water. The data of analyzed samples of all grades of AQOAT polymers as disclosed in Table 2 on page 13 of WO 2011/159626 are listed below.

| Item | Substituent | L Grades Range* | L Grades Average (of 12 lots) | M Grades Range* | M Grades Average (of 28 lots) | H Grades Range* | H Grades Average (of 17 lots) |
|---|---|---|---|---|---|---|---|
| Manufacturer's Certificate of Analysis (wt %) | Methoxyl | 21.7-22.5 | 22.1 ± 0.3 | 22.7-23.6 | 23.1 ± 0.2 | 23.2-24.1 | 23.7 ± 0.3 |
| | Hydroxy-propoxyl | 6.8-7.1 | 7.0 ± 0.1 | 7.0-7.9 | 7.3 ± 0.2 | 7.1-7.8 | 7.5 ± 0.2 |
| | Acetyl | 7.2-8.1 | 7.7 ± 0.3 | 8.7-10.8 | 9.3 ± 0.4 | 11.0-112.2 | 11.5 ± 0.3 |
| | Succinoyl | 15.1-16.5 | 15.5 ± 0.4 | 10.8-11.5 | 11.2 ± 0.2 | 5.3-7.6 | 6.5 ± 0.7 |
| Calculated Degree of Substitution** | DOSM | 1.84-1.91 | 1.87 ± 0.03 | 1.85-1.94 | 1.89 ± 0.02 | 1.84-1.92 | 1.88 ± 0.02 |
| | DOSHP | 0.24-0.25 | 0.25 ± 0.01 | 0.24-0.27 | 0.25 ± 0.01 | 0.23-0.26 | 0.24 ± 0.01 |
| | DOSAc | 0.44-0.49 | 0.47 ± 0.02 | 0.51-0.65 | 0.55 ± 0.03 | 0.62-0.70 | 0.66 ± 0.02 |
| | DOSs | 0.39-0.43 | 0.40 ± 0.01 | 0.27-0.29 | 0.28 ± 0.01 | 0.13-0.19 | 0.16 ± 0.02 |
| | DOSM + DOSAc + DOSs | 2.70-2.80 | 2.75 ± 0.03 | 2.65-2.87 | 2.71 ± 0.03 | 2.63-2.73 | 2.70 ± 0.03 |
| | DOSAc + DOSs | 0.85-0.89 | 0.88 ± 0.01 | 0.80-0.93 | 0.83 ± 0.03 | 0.77-0.84 | 0.81 ± 0.02 |

*Range of several lots of polymer for each grade (the number of lots is indicated under "Average").
**Degree of substitution calculated as described in WO 2011/159626

The properties of the HPMCAS of Examples 1-27, Comparative Examples A-E, Comparative Examples CE-11 to CE-16 and Comparative Examples CE-C, CE-D, CE-E and CE-H to CE-J are listed in Table 2 below. In Table 2 the abbreviations have the following meanings:

$DS_M$=DS(methoxyl): degree of substitution with methoxyl groups;

$MS_{HP}$=MS(hydroxypropoxyl): molar subst. with hydroxypropoxyl groups;

$DS_{Ac}$: degree of substitution of acetyl groups;

$DS_s$: degree of substitution of succinoyl groups.

TABLE 1

| (Comp.) Example | HPMC* g | HPMC* Mol | HPMC, 2% viscosity in water (mPa·s) | Glacial acetic acid g | Glacial acetic acid HPMC | Succinic anhydride g | Succinic anhydride mol/mol HPMC | Acetic anhydride g | Acetic anhydride mol/mol HPMC | Sodium acetate g | Sodium acetate mol/mol HPMC | Reaction temperature (°C.) | Reaction time, hours | Temperature of washing water, °C. |
|---|---|---|---|---|---|---|---|---|---|---|---|---|---|---|
| 1 | 195 | 0.96 | 3.0 | 440 | 7.6 | 35 | 0.36 | 180 | 1.91 | 0 | 0 | 85 | 3 | 95 |
| 2 | 195 | 0.96 | 3.0 | 400 | 6.9 | 35 | 0.36 | 180 | 1.91 | 0 | 0 | 85 | 3 | 95 |
| 3 | 195 | 0.96 | 3.0 | 300 | 5.2 | 35 | 0.36 | 180 | 1.91 | 0 | 0 | 85 | 3 | 95 |
| 4 | 195 | 0.96 | 3.0 | 200 | 3.5 | 35 | 0.36 | 180 | 1.91 | 0 | 0 | 85 | 3 | 95 |
| 5 | 195 | 0.96 | 3.0 | 100 | 1.7 | 35 | 0.36 | 180 | 1.91 | 0 | 0 | 85 | 3 | 95 |
| 6 | 195 | 0.96 | 3.0 | 500 | 8.7 | 50 | 0.52 | 150 | 1.59 | 0 | 0 | 85 | 3 | 95 |
| 7 | 195 | 0.96 | 3.0 | 400 | 6.9 | 50 | 0.52 | 100 | 1.06 | 0 | 0 | 85 | 3 | 95 |
| 8 | 195 | 0.96 | 3.0 | 400 | 6.9 | 70 | 0.73 | 80 | 0.85 | 0 | 0 | 85 | 3 | 95 |
| 9 | 195 | 0.96 | 3.0 | 400 | 6.9 | 70 | 0.73 | 50 | 0.53 | 0 | 0 | 85 | 3 | 95 |
| 10 | 195 | 0.96 | 3.0 | 400 | 6.9 | 50 | 0.52 | 100 | 1.06 | 0 | 0 | 85 | 4.5 | 95 |

TABLE 1-continued

| (Comp.) Example | HPMC* g | HPMC* Mol | HPMC, 2% viscosity in water (mPa·s) | Glacial acetic acid g | Glacial acetic acid mol/mol HPMC | Succinic anhydride g | Succinic anhydride mol/mol HPMC | Acetic anhydride g | Acetic anhydride mol/mol HPMC | Sodium acetate g | Sodium acetate mol/mol HPMC | Reaction temperature (°C.) | Reaction time, hours | Temperature of washing water, °C. |
|---|---|---|---|---|---|---|---|---|---|---|---|---|---|---|
| 11 | 195 | 0.96 | 3.0 | 100 | 1.7 | 50 | 0.52 | 150 | 1.59 | 0 | 0 | 85 | 3 | 95 |
| 12 | 195 | 0.96 | 3.0 | 100 | 1.7 | 50 | 0.52 | 100 | 1.06 | 0 | 0 | 85 | 3 | 95 |
| 13 | 195 | 0.96 | 3.0 | 100 | 1.7 | 70 | 0.73 | 70 | 0.74 | 0 | 0 | 85 | 3 | 95 |
| 14 | 195 | 0.96 | 3.0 | 100 | 1.7 | 50 | 0.52 | 150 | 1.59 | 0 | 0 | 85 | 4.5 | 95 |
| 15 | 195 | 0.96 | 3.0 | 100 | 1.7 | 50 | 0.52 | 150 | 1.59 | 0 | 0 | 90 | 4 | 95 |
| 16 | 195 | 0.96 | 3.0 | 100 | 1.7 | 50 | 0.52 | 150 | 1.59 | 0 | 0 | 90 | 5 | 95 |
| 17 | 195 | 0.96 | 3.0 | 100 | 1.7 | 50 | 0.52 | 150 | 1.59 | 0 | 0 | 90 | 6 | 95 |
| 18 | 195 | 0.96 | 3.0 | 100 | 1.7 | 100 | 1.04 | 300 | 3.18 | 0 | 0 | 90 | 3 | 95 |
| 19 | 195 | 0.96 | 3.0 | 100 | 1.7 | 100 | 1.04 | 300 | 3.18 | 0 | 0 | 90 | 6 | 21 |
| 20 | 195 | 0.96 | 3.0 | 50 | 0.9 | 50 | 0.52 | 150 | 1.59 | 0 | 0 | 90 | 6 | 21 |
| 21 | 195 | 0.96 | 3.0 | 150 | 2.6 | 50 | 0.52 | 150 | 1.59 | 0 | 0 | 90 | 6 | 21 |
| 22 | 195 | 0.96 | 3.0 | 200 | 3.5 | 50 | 0.52 | 150 | 1.59 | 0 | 0 | 90 | 6 | 21 |
| 23 | 195 | 0.96 | 3.0 | 250 | 4.4 | 50 | 0.52 | 150 | 1.59 | 0 | 0 | 90 | 6 | 21 |
| 23A | 195 | 0.96 | 3.0 | 250 | 4.4 | 50 | 0.52 | 150 | 1.59 | 0 | 0 | 90 | 6 | 95 |
| A | 195 | 0.96 | 3.0 | 300 | 5.2 | 50 | 0.52 | 150 | 1.59 | 100 | 1.27 | 90 | 4 | 71 |
| B | 195 | 0.96 | 3.0 | 300 | 5.2 | 50 | 0.52 | 150 | 1.59 | 100 | 1.27 | 90 | 5 | 21 |
| C | 195 | 0.96 | 3.0 | 300 | 5.2 | 50 | 0.52 | 150 | 1.59 | 100 | 1.27 | 90 | 6 | 21 |
| D | 195 | 0.96 | 3.0 | 400 | 6.9 | 50 | 0.52 | 150 | 1.59 | 100 | 1.27 | 90 | 4 | 21 |
| E | 195 | 0.96 | 3.0 | 300 | 5.2 | 50 | 0.52 | 150 | 1.59 | 50 | 0.63 | 90 | 4 | 21 |
| 24 | 195 | 0.96 | 3.0 | 100 | 1.7 | 100 | 1.04 | 300 | 3.18. | 0 | 0 | 95 | 6 | 21 |
| 25 | 195 | 0.96 | 3.0 | 100 | 1.7 | 100 | 1.04 | 330 | 3.50 | 0 | 0 | 90 | 6 | 21 |
| 26 | 195 | 0.96 | 3.0 | 100 | 1.7 | 100 | 1.04 | 360 | 3.82 | 0 | 0 | 90 | 6 | 21 |
| 27 | 195 | 0.96 | 3.0 | 100 | 1.7 | 100 | 1.04 | 400 | 4.24 | 0 | 0 | 90 | 6 | 21 |
| CE-11 | 215 | 1.06 | 1.5 | 231 | 3.6 | 35.5 | 0.33 | 130 | 1.25 | 86.9 | 1.00 | 85 | 3.5 | 21 |
| CE-12 | 60 | 0.3 | 1.39 | 35 | 2.0 | 10.1 | 0.34 | 37.2 | 1.28 | 17.4 | 0.72 | 85 | 3.5 | 21 |
| CE-13 | 60 | 0.3 | 1.39 | 30 | 1.7 | 10.1 | 0.34 | 37.2 | 1.28 | 17.4 | 0.72 | 85 | 3.5 | 21 |
| CE-14 | 100 | 0.49 | 2.0 | 135 | 4.5 | 16.9 | 0.34 | 62 | 1.28 | 41.4 | 1.02 | 85 | 3.5 | 71 |
| CE-15 | 100 | 0.49 | 2.0 | 126 | 4.3 | 16.9 | 0.34 | 62 | 1.28 | 41.4 | 1.02 | 85 | 3.5 | 21 |
| CE-16 | 100 | 0.49 | 2.0 | 117 | 4.0 | 16.9 | 0.34 | 62 | 1.28 | 41.4 | 1.02 | 85 | 3.5 | 21 |
| CE-C | 150 | 0.74 | 3.0 | 450 | 10.1 | 35.8 | 0.48 | 57.4 | 0.79 | 59.57 | 0.98 | 85 | 3.5 | 21 |
| CE-D | 195 | 0.97 | 3.1 | 442 | 7.6 | 54.6 | 0.57 | 254 | 2.69 | 195 | 2.47 | 85 | 3.5 | 21 |
| CE-E | 200 | 0.96 | 3.1 | 600 | 10.2 | 50.0 | 0.51 | 76 | 0.78 | 160 | 1.97 | 3.5 | 2.4 | 21 |

*Calculated on a dried basis

TABLE 2

| (Comparative) Ex. | Molecular weight (kDA) $M_n$ | Molecular weight (kDA) $M_w$ | 10% viscosity in acetone [mPa·s] | 2% viscosity in NaOH [mPa·s] | Methoxyl (%) | Hydroxypropoxyl (%) | Acetyl (%) | Succinoyl (%) | $DS_M$ | $MS_{HP}$ | $DS_{Ac}$ | $DS_S$ | Sum $DS_{Ac}$ + $DS_S$ | % water-soluble at 2.5% | Water-soluble at 2% |
|---|---|---|---|---|---|---|---|---|---|---|---|---|---|---|---|
| 1 | 25 | 89 | 12.0 | 4.3 | 26.8 | 8.5 | 7.1 | 2.1 | 1.93 | 0.26 | 0.37 | 0.05 | 0.42 | 99 | yes* |
| 2 | 25 | 114 | 13.0 | 3.8 | 26.4 | 8.3 | 7.6 | 2.1 | 1.91 | 0.25 | 0.40 | 0.05 | 0.45 | 100 | yes |
| 3 | 21 | 64 | 14.0 | 3.5 | 26.5 | 8.2 | 7.3 | 2.5 | 1.92 | 0.25 | 0.38 | 0.06 | 0.44 | 100 | yes* |
| 4 | 18 | 31 | n.m. | 3.3 | 26.4 | 8.1 | 6.8 | 3.0 | 1.91 | 0.24 | 0.35 | 0.07 | 0.42 | 100 | yes* |
| 5 | 17 | 39 | n.m. | 3.1 | 26.0 | 7.9 | 7.3 | 4.2 | 1.92 | 0.24 | 0.39 | 0.10 | 0.49 | 100 | yes |
| 6 | 18 | 29 | n.m. | 3.4 | 26.8 | 8.2 | 6.8 | 2.6 | 1.93 | 0.24 | 0.35 | 0.06 | 0.41 | 100 | yes* |
| 7 | 20 | 27 | n.m. | n.m. | 27.4 | 8.3 | 5.3 | 3.5 | 1.97 | 0.25 | 0.28 | 0.08 | 0.36 | 99 | yes* |
| 8 | 20 | 27 | n.m. | n.m. | 27.3 | 8.3 | 4.1 | 5.0 | 1.97 | 0.25 | 0.21 | 0.11 | 0.32 | 101 | yes* |
| 9 | 20 | 26 | n.m. | n.m. | 27.8 | 8.3 | 2.4 | 5.9 | 1.99 | 0.25 | 0.12 | 0.13 | 0.25 | 101 | yes* |
| 10 | 18 | 26 | n.m. | n.m. | 26.6 | 8.2 | 6.1 | 4.3 | 1.95 | 0.25 | 0.32 | 0.10 | 0.42 | 101 | yes* |
| 11 | 20 | 52 | n.m. | n.m. | 25.6 | 7.9 | 6.8 | 6.6 | 1.93 | 0.25 | 0.37 | 0.15 | 0.52 | 101 | yes |
| 12 | 22 | 57 | n.m. | n.m. | 25.1 | 7.9 | 5.3 | 8.3 | 1.90 | 0.25 | 0.29 | 0.19 | 0.48 | 100 | yes |
| 13 | 23 | 57 | n.m. | n.m. | 24.8 | 7.7 | 3.2 | 11.4 | 1.89 | 0.24 | 0.18 | 0.27 | 0.45 | 100 | yes |
| 14 | 20 | 47 | n.m. | n.m. | 25.1 | 7.9 | 6.7 | 6.6 | 1.89 | 0.24 | 0.36 | 0.15 | 0.52 | 100 | yes |
| 15 | 29 | 74 | n.m. | n.m. | 24.3 | 7.7 | 7.8 | 7.2 | 1.86 | 0.24 | 0.43 | 0.17 | 0.60 | 100 | yes |
| 16 | 27 | 67 | n.m. | n.m. | 24.2 | 7.7 | 8.0 | 7.5 | 1.86 | 0.24 | 0.44 | 0.18 | 0.62 | 96 | yes |
| 17 | 30 | 87 | n.m. | n.m. | 24.2 | 7.7 | 8.3 | 7.6 | 1.87 | 0.25 | 0.46 | 0.18 | 0.64 | 95 | yes |
| 18 | 32 | 68 | n.m. | n.m. | 24.0 | 7.8 | 7.9 | 6.7 | 1.82 | 0.24 | 0.43 | 0.16 | 0.59 | 97 | yes |
| 19 | 36 | 92 | n.m. | n.m. | 23.1 | 7.8 | 9.0 | 7.6 | 1.80 | 0.25 | 0.50 | 0.18 | 0.68 | 79 | part. |
| 20 | 58 | 176 | n.m. | n.m. | 24.2 | 7.7 | 7.3 | 8.4 | 1.87 | 0.25 | 0.41 | 0.20 | 0.61 | 81 | part. |
| 21 | 31 | 64 | n.m. | n.m. | 24.2 | 7.7 | 8.7 | 6.6 | 1.86 | 0.24 | 0.48 | 0.16 | 0.64 | 97 | yes |
| 22 | 29 | 57 | n.m. | n.m. | 23.8 | 7.7 | 9.4 | 5.9 | 1.82 | 0.24 | 0.52 | 0.14 | 0.66 | 99 | yes |
| 23 | 28 | 52 | n.m. | n.m. | 24 | 8 | 9.5 | 5.1 | 1.83 | 0.25 | 0.52 | 0.12 | 0.64 | 99 | yes |
| 23A | 17 | 33 | n.m. | n.m. | 25.4 | 8 | 8.9 | 4.8 | 1.93 | 0.25 | 0.49 | 0.11 | 0.60 | 98 | yes |
| A | 139 | 356 | 118 | n.m. | 22.0 | 6.9 | 9.2 | 14.9 | 1.88 | 0.24 | 0.57 | 0.39 | 0.96 | 10 | no |
| B | 108 | 293 | 122 | n.m. | 22.1 | 6.9 | 9.6 | 14.5 | 1.89 | 0.24 | 0.59 | 0.38 | 0.97 | 4 | no |

TABLE 2-continued

| (Comparative) Ex. | Molecular weight (kDA) | | 10% viscosity in acetone [mPa·s] | 2% viscosity in NaOH [mPa·s] | Methoxyl (%) | Hydroxypropoxyl (%) | Acetyl (%) | Succinoyl (%) | $DS_M$ | $MS_{HP}$ | $DS_{Ac}$ | $DS_S$ | Sum $DS_{Ac}$ + $DS_S$ | % water-soluble at 2.5% | Water-soluble at 2% |
|---|---|---|---|---|---|---|---|---|---|---|---|---|---|---|---|
| | $M_n$ | $M_w$ | | | | | | | | | | | | | |
| C | 112 | 293 | 169 | n.m. | 21.5 | 6.8 | 9.4 | 14.3 | 1.82 | 0.24 | 0.57 | 0.37 | 0.94 | 6 | no |
| D | 29 | 80 | 15.8 | n.m. | 22.9 | 7.2 | 7.9 | 13.3 | 1.89 | 0.25 | 0.47 | 0.34 | 0.81 | 51 | no |
| E | 56 | 164 | 21.7 | n.m. | 22.5 | 7.1 | 8.4 | 13.9 | 1.88 | 0.25 | 0.51 | 0.36 | 0.86 | 30 | no |
| 24 | 22 | 65 | 23 | n.m. | 24.1 | 7.7 | 9.3 | 7.4 | 1.89 | 0.25 | 0.52 | 0.18 | 0.70 | 83 | part. |
| 25 | 23 | 60 | 122 | n.m. | 24.4 | 7.7 | 8.4 | 6.6 | 1.87 | 0.24 | 0.46 | 0.16 | 0.62 | 85 | part. |
| 26 | 27 | 73 | 479 | n.m. | 24.0 | 7.8 | 8.8 | 6.3 | 1.84 | 0.25 | 0.49 | 0.15 | 0.64 | 88 | part. |
| 27 | 22 | 64 | 89 | n.m. | 24.7 | 7.7 | 8.7 | 5.5 | 1.87 | 0.24 | 0.48 | 0.13 | 0.60 | 90 | yes |
| CE-11 | 11 | 24 | 1.97 | 1.60 | 23.1 | 7.8 | 10.0 | 11.3 | 1.93 | 0.27 | 0.60 | 0.29 | 0.89 | 71 | no |
| CE-12 | 10 | 41 | 1.81 | 1.49 | 22.7 | 7.7 | 9.8 | 12.3 | 1.91 | 0.27 | 0.59 | 0.32 | 0.91 | 50 | no |
| CE-13 | 12 | 112 | 2.41 | 1.49 | 22.7 | 7.7 | 10.2 | 11.6 | 1.90 | 0.27 | 0.62 | 0.30 | 0.92 | 51 | no |
| GE-14 | 16 | 68 | 7.9 | 2.0 | 23.4 | 7.8 | 9.1 | 11.5 | 1.94 | 0.27 | 0.54 | 0.29 | 0.83 | 62 | no |
| CE-15 | 20 | 105 | 8.5 | 2.0 | 23.3 | 7.8 | 9.4 | 11.7 | 1.94 | 0.27 | 0.56 | 0.30 | 0.86 | 51 | no |
| CE-16 | 28 | 158 | 10.4 | 2.0 | 23.1 | 7.9 | 9.3 | 11.4 | 1.91 | 0.27 | 0.56 | 0.29 | 0.85 | 43 | no |
| CE-C | 53 | 23 | n.m. | 2.90 | 23.7 | 7.6 | 5.8 | 14.7 | 1.96 | 0.26 | 0.35 | 0.37 | 0.72 | 67 | no |
| CE-D | 36 | 139 | 37.4 | 2.61 | 22.7 | 7.5 | 11.0 | 12.1 | 1.94 | 0.26 | 0.68 | 0.32 | 1.00 | 11 | no |
| CE-E | 26 | 65 | 16.6 | 2.89 | 22.9 | 7.3 | 5.7 | 16.0 | 1.91 | 0.25 | 0.34 | 0.41 | 0.75 | 51 | no |
| CE-H | 33 | 153 | 27.7 | 3.0 | 22.5 | 7.0 | 8.1 | 14.7 | 1.90 | 0.24 | 0.49 | 0.38 | 0.87 | 12 | no |
| CE-I | 27 | 114 | 26.5 | 2.94 | 23.1 | 7.3 | 9.3 | 10.6 | 1.88 | 0.24 | 0.54 | 0.26 | 0.76 | 45 | no |
| CE-J | 29 | 137 | 29.8 | 2.89 | 23.6 | 7.2 | 11.6 | 7.9 | 1.90 | 0.24 | 0.67 | 0.19 | 0.86 | 31 | no | nm: not measured
*very clear solution
part: partially

The esterified cellulose ethers of Examples 1-27 were dissolved at a concentration of 2 wt.-% in water at a temperature of 5° C. (for the qualitative determination of the water-solubility) or at a temperature of 2° C., respectively (for the quantitative determination of the water-solubility). When the temperature of the prepared HPMCAS solution in water was increased to 20° C. (room temperature), no precipitation occurred. FIG. 1 represents a photograph of 2 wt.-% solutions of the HPMCAS of Examples 7-11 in water after the temperature of the solution was increased to 20° C.

Gelation

Figure 2:
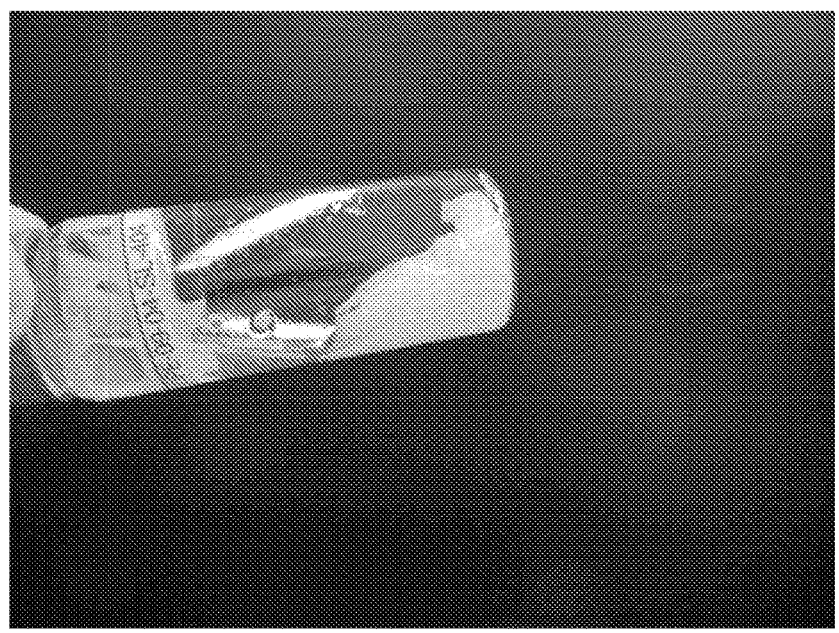
FIG. 2 is a photographical representation of a solution of the esterified cellulose ether of Example 23 in water while the solution is in the process of being gelled at 40° C.

Aqueous solutions of HPMCAS having a total degree of ester substitution of from 0.10 to 0.65 and particularly from 0.20 to 0.65 gel at slightly elevated temperature, typically at 30 to 55° C. FIG. 2 is a photographical representation of a 2 wt.-% solution of the HPMCAS of Example 23 in water while the solution is in the process of being gelled at 40° C. FIG. 3 is a photographical representation of a 5.45 wt.-% solution of the HPMCAS of Example 18 in water after the solution has been gelled at 40° C. A glass bottle containing the gelled HPMCAS can be turned upside down without causing the gelled HPMCAS to flow. The 5.45 wt.-% solution has a low viscosity at 5° C. (233 mPa·s, measured using a Haake RS 600 rheometer in a cup and bob geometry (CC-25) at 10 sec$^{-1}$) which allows convenient processing. Rheology measurements were carried out to measure the gelation temperatures and gel strength according to the storage modulus G' at 55° C. of 2 wt.-% solutions of the HPMCAS of Examples 1 and 3-27 in water as described further above. The results are listed in Table 3 below.

TABLE 3

| Ex. | Gel. Temp., ° C. | Gel Strength G' at 55° C., Pa |
|---|---|---|
| 1 | 40 | 136 |
| 3 | 39 | 121 |
| 4 | 38 | 112 |
| 5 | 36 | 99 |
| 6 | 40 | 67 |
| 7 | 43 | 84 |
| 8 | 43 | 69 |
| 9 | 47 | 23 |
| 10 | 39 | 87 |
| 11 | 33 | 118 |
| 12 | 33 | 113 |
| 13 | 33 | 109 |
| 14 | 34 | 103 |
| 15 | 32 | 189 |
| 16 | 32 | 281 |
| 17 | 31 | 203 |
| 18 | 40 | 33 |
| 19 | No gel | <1 |
| 20 | 33 | 120 |
| 21 | 34 | 91 |
| 22 | 36 | 80 |
| 23 | 39 | 42 |
| 23A | 31 | 100 |
| 24 | 44 | 14 |
| 25 | 45 | 65 |
| 26 | 32 | 73 |
| 27 | 45 | 32 |

For comparative purposes a commercially available HPMCAS was neutralized with $NH_4HCO_3$ to adjust its pH to 6.3. The HPMCAS had 23.5% methoxyl groups ($DS_{methoxyl}$=1.93), 7.3% hydroxypropoxyl groups ($MS_{hydroxypropoxyl}$=0.25), 9.8% acetyl groups ($DS_{acetyl}$=0.58), 10.5% succinoyl groups ($DS_{succinoyl}$=0.26), and a viscosity of 2.9 mPa·s, measured as a 2.0% by weight solution of the HPMCAS in 0.43 wt. % aqueous NaOH. 2 and 5 wt.-% solutions of the HPMCAS in water were prepared. When preparing 100 g of a 2 wt.-% solution of HPMCAS in water, 0.19 g of $NH_4HCO_3$ was used for neutralization; the resulting degree neutralization of the HPMCAS was 96%. When preparing 100 g of a 5 wt.-% solution of HPMCAS in water, 0.43 g of $NH_4HCO_3$ was used for neutralization; the resulting degree neutralization of the HPMCAS was 87%. Rheology measurements were carried out to measure the gelation temperatures and gel strength according to the storage modulus G' at 55° C. as described further. No gelling occurred.

Preparation of Capsules from Water Soluble HPMCAS of Example 15

An aqueous solution of 9.0 wt.-% of the water soluble HPMCAS of Example 15 was prepared by dissolving the HPMCAS in deionized water at a temperature of 2° C. Triethylcitrate was added as a plasticizer at an amount of 33 wt.-%, based on the weight of the HPMCAS. Capsule shells were produced by dipping metallic pins having a temperature of 21° C., 30° C. and 55° C. respectively, into the HPMCAS solution having a temperature of 8° C. The pins were then withdrawn from the aqueous HPMCAS solution and a film was formed on the molding pins. Capsule shells of good quality formed on the pins at each of these temperatures. FIGS. 4A, 5A and 6A are photographical representations of capsule shells on metallic pins having a temperature of 21° C., 30° C. and 55° C., respectively. The capsule shells formed on pins having room temperature (21° C.) were dried at room temperature, the capsule shells formed on pins having a temperature of 30° C. were dried at 30° C. and the capsule shells formed on pins having a temperature of 55° C. were dried at 55° C. FIGS. 4B, 5B and 6B are photographical representations of pieces of capsule shells formed on metallic pins having a temperature of 21° C., 30° C. and 55° C., respectively, after the capsule shells have been removed from the dipping pins.

Figure 4C:
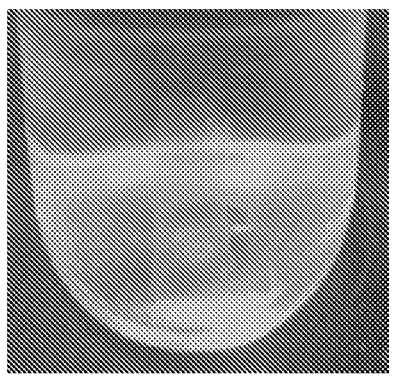
FIGS. 4C, 5C and 6C are photographical representations of non-dissolved pieces of capsule shells in 0.1 N HCl. The pieces of capsule shells are small pieces of the capsules shells represented in FIGS. 4B, 5B and 6B, respectively.
Figure 5C:
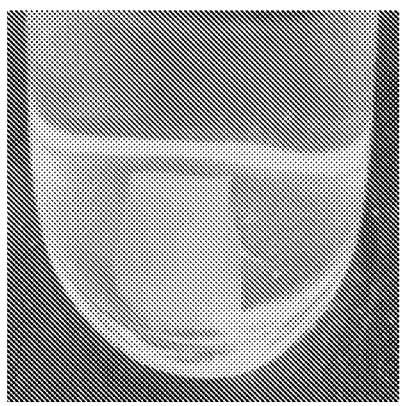
Figure 6C:
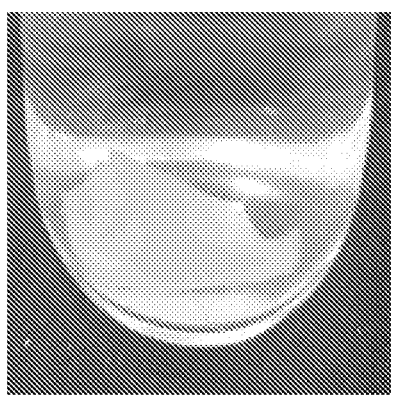

To test the solubility of the capsule shells in the acidic environment of the stomach, the capsule shells were broken into pieces and immersed into 0.1 N HCl. The capsule pieces were left there for 12 h at a temperature of 21° C. The capsule pieces did not dissolve in 0.1 N HCl during these 12 hours. The capsule pieces could be seen by the unprotected eye in 0.1 N HCl during these entire 12 hours. FIGS. 4C, 5C and 6C are photographical representations of non-dissolved pieces of capsule shells in 0.1 N HCl. The pieces of capsule shells are small pieces of the capsules shells represented in FIGS. 4B, 5B and 6B, respectively.

Figure 4D:
FIGS. 4D, 5D and 6D are photographical representations of an aqueous buffer solution of pH 6.8 into which the non-dissolved pieces of capsule shells shown in FIGS. 4C, 5C and 6C have been placed; all pieces of capsule shells are dissolved in the aqueous buffer solution of pH 6.8.
Figure 5D:
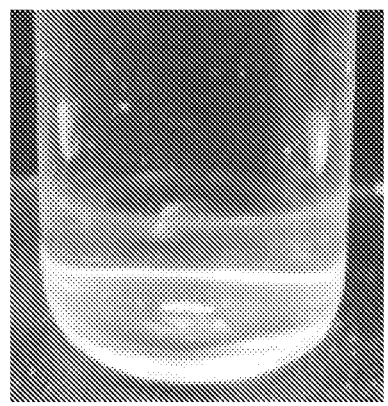
Figure 6D:
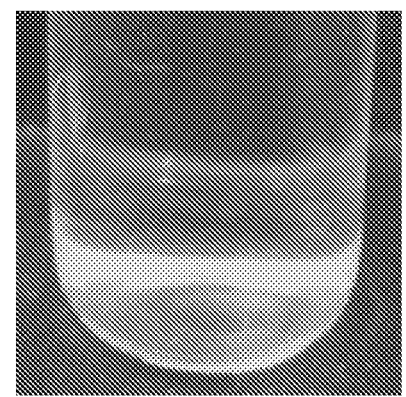

To test the solubility of the capsule shells in a neutral environment, the 0.1 N HCl was poured off from the capsule pieces and the capsule pieces were put into a McIvaine's buffer solution (containing disodium monophosphate and citric acid) having a pH of 6.8. After about 60 minutes all pieces of capsule shells were completely dissolved in the buffer of pH 6.8 leaving clear solutions. FIGS. 4D, 5D and 6D are photographical representations of an aqueous buffer solution of pH 6.8 into which the non-dissolved pieces of capsule shells shown in FIGS. 4C, 5C and 6C have been placed; all pieces of capsule shells are dissolved in the aqueous buffer solution of pH 6.8.

Preparation of Capsules from Water Soluble HPMCAS of Example 23

An aqueous solution of 7.5 wt.-% of the water soluble HPMCAS of Example 23 was prepared by dissolving the HPMCAS in deionized water at a temperature of 2° C. Triethylcitrate was added as a plasticizer at an amount of 20 wt.-%, based on the weight of the HPMCAS. Capsule shells were produced by dipping metallic pins having a temperature of 80° C., into the HPMCAS solution having a temperature of 10° C. The capsule shells formed on the pins were dried at 80° C. The prepared capsule shells had the same appearance and showed the same solubility properties in 0.1 N HCl and in aqueous buffer solution of pH 6.8 as the capsules prepared from the HPMCAS of Example 15.

The invention claimed is:

1. A hydroxypropyl methyl cellulose acetate succinate comprising acetyl groups and succinoyl groups, wherein
    i) the degree of neutralization of the succinoyl groups is not more than 0.4,
    ii) the total degree of ester substitution is from 0.10 to 0.70, and
    iii) the hydroxypropyl methyl cellulose acetate succinate has a solubility in water of at least 2.0 weight percent at 2° C.

2. The hydroxypropyl methyl cellulose acetate succinate of claim 1 wherein the total degree of ester substitution is from 0.20 to 0.60.

3. The hydroxypropyl methyl cellulose acetate succinate of claim 1 having a degree of substitution of acetyl groups of from 0.25 to 0.69 or a degree of substitution of succinoyl groups of from 0.05 to 0.45.

4. The hydroxypropyl methyl cellulose acetate succinate of claim 1 wherein at least 85 wt. % of the hydroxypropyl methyl cellulose acetate succinate is soluble in a mixture of 2.5 weight parts of the hydroxypropyl methyl cellulose acetate succinate and 97.5 weight parts of water at 2° C.

5. The hydroxypropyl methyl cellulose acetate succinate of claim 4 wherein at least 90 wt. % of the hydroxypropyl methyl cellulose acetate succinate is soluble in a mixture of 2.5 weight parts of the hydroxypropyl methyl cellulose acetate succinate and 97.5 weight parts of water at 2° C.

6. An aqueous composition comprising the hydroxypropyl methyl cellulose acetate succinate of claim 1 dissolved in an aqueous liquid.

7. The aqueous composition of claim 6 comprising at least 10 weight percent of dissolved esterified cellulose ether, based on the total weight of the aqueous composition.

8. A liquid composition comprising at least one hydroxypropyl methyl cellulose acetate succinate of claim 1 and an organic diluent.

9. A process for coating a dosage form comprising the step of contacting an aqueous composition comprising the hydroxypropyl methyl cellulose acetate succinate of claim 1 dissolved in an aqueous liquid with the dosage form.

10. A process for the manufacture of capsule shells comprising the step of contacting an aqueous composition comprising the hydroxypropyl methyl cellulose acetate succinate of claim 1 dissolved in an aqueous liquid with dipping pins.

11. A coated dosage form wherein the coating comprises at least one hydroxypropyl methyl cellulose acetate succinate of claim 1.

12. A polymeric capsule shell comprising at least one hydroxypropyl methyl cellulose acetate succinate of claim 1.

13. A capsule comprising a capsule shell of claim 12 and further comprising a drug or a nutritional or food supplement or a combination thereof.

14. A solid dispersion of at least one active ingredient in at least one hydroxypropyl methyl cellulose acetate succinate of claim 1.

* * * * *